US006830932B1

(12) United States Patent
Danne et al.

(10) Patent No.: US 6,830,932 B1
(45) Date of Patent: Dec. 14, 2004

(54) IN-VITRO METHOD FOR DETECTING AND DIAGNOSING ACUTE CORONARY SYNDROMES

(76) Inventors: Oliver Danne, Döberitzer Weg 11, 114476 Seeburg (DE); Ulrich Frei, Paulstr. 23, 10557 Berlin (DE); Adolf Zschunke, Peltzerweg 10, 12527 Berlin (DE); Clemens Mügge, Achtermann Str. 57, 13187 Berlin (DE)

(*) Notice: Subject to any disclaimer, the term of this patent is extended or adjusted under 35 U.S.C. 154(b) by 0 days.

(21) Appl. No.: 09/762,691
(22) PCT Filed: Aug. 11, 1999
(86) PCT No.: PCT/EP99/05911
§ 371 (c)(1), (2), (4) Date: Feb. 9, 2001
(87) PCT Pub. No.: WO00/10014
PCT Pub. Date: Feb. 24, 2000

(30) Foreign Application Priority Data

Aug. 12, 1998 (DE) .......................................... 198 36 617

(51) Int. Cl.$^7$ .............................................. G01N 33/00
(52) U.S. Cl. ......................................... 436/86; 436/811
(58) Field of Search .................................... 436/86, 811

(56) References Cited

U.S. PATENT DOCUMENTS 3,401,086 A   9/1968 Hoffmann et al.
5,747,274 A * 5/1998 Jackowski .................. 435/7.94

OTHER PUBLICATIONS

Williams et al., "Calcim–independent phospholipase A2 mediates CREB phosphorylation and c–fos expression during ischemia", Am. J. Physiol. Heart Circ. Physiol, 281: H168–H176, 2001.*

Higuchi et al., 'Mapping of Lactate and N–Acetyl–L–aspartate Predicts Infarction during Acute Focal Ischemia: In Vivo $^1$H Magnetic Resonance Spectroscopy in Rats,' Neurosurgery, 38(1):121–30 (Jan. 1996).

Langton et al., 'Serum phospholipase $A_2$ and lysolecithin changes following myocardial infarction,' Clinica Chimica Acta, 205:223–31 (1992).

(List continued on next page.)

Primary Examiner—Jill Warden
Assistant Examiner—Monique T. Cole
(74) Attorney, Agent, or Firm—Kreigsman & Kreigsman

(57) ABSTRACT

The invention relates to an in vitro method of recognizing acute coronary syndroms, especially an acute myocardial infarction, by determining and evaluating the content of choline, choline and/or trimethyl ammonium derivatives selected from the group comprising phosphoryl choline, plasmalogens, and lysoplasmenyl choline, and/or the reaction products thereof selected from the group comprising 1-O-alk-1'-enyl-2 substituted glycerol and 1-O-alk-1'-enyl-2 substituted glycerol phosphate in body fluids or component parts of the body, said method comprising the following steps:

drawing a sample of a suitable body fluid or component part of the body; determining the content of choline, choline and/or trimethyl ammonium derivatives selected from the group comprising phosphoryl choline, plasmalogens, and lysoplasmenyl choline, and/or the reaction products thereof selected from the group comprising 1-O-alk-1'-enyl-2 substituted glycerol and 1-O-alk-1'-enyl-2 substituted glycerol phosphate by a suitable method of determination (nuclear magnetic resonance methods, biochemical, enzymatic, immunological, clinical-chemical, chromatographic, mass spectrometric, electrochemical, photometric methods, or other methods); and evaluating the measured results, taking into account a limit value for recognition or exclusion of acute coronary syndroms, especially an acute myocardial infarction.

14 Claims, 6 Drawing Sheets

OTHER PUBLICATIONS

Lauriero et al., '$^{99}$Tc$^m$–HMPAO SPET and $^1$H–MRS (proton magnetic resonance spectroscopy) in patients with ischaemic cerebral infarction,' Nuclear Medicine Communications, 17:140–6 (1996).

Danne et al., 'Prognostic Implications of Elevated Whole Blood Choline Levels in Acute Coronary Syndromes,' Am J Cardiol, 91:1060–7 (May 1, 2003).

The Joint European Society of Cardiology/American College of Cardiology Committee, 'Myocardial Infarction Redefined–A Consensus Document of The Joint European Society of Cardiology/American College of Cardiology Committee for the Redefinition of Myocardial Infarction,' Journal of the American College of Cardiology, 36(3):959–69 (2000).

Chierchia, 'Current therapeutic strategies in unstable angina,' European Heart Journal Supplements, 1(Supplement N) :N2–N6 (1999).

Ryan et al., 'ACC/AHA Guidelines for the Management of Patients With Acute Myocardial Infarction,' JACC, 28(5):1328–428 (1996).

Ohman et al., 'Cardiac Troponin T Levels for Risk Stratification in Acute Myocardial Ischemia,' The New England Journal of Medicine, 335(18):1333–41 (1996).

Van Miltenburg–van Zijl et al., 'Incidence and Follow–Up of Braunwald Subgroups in Unstable Angina Pectoris,' JACC, 25(6):1286–92 (1995).

Groenendaal et al., 'Proton Magnetic Resonance Spectroscopic Imaging in Neonatal Stroke,' Neuropediatrics, 26:243–8 (1995).

'Unstable Angina: Diagnosis and Management,' Clinical Practice Guideline No. 10, AHCPR Publication No. 94–0602: May 1994 (Amended).

Braunwald et al., 'Diagnosing and Managing Unstable Angina,' Circulation, 90(1):613–22 (1994).

Corr et al., 'Lysophosphoglycerides and Ventricular Fibrillation Early After Onset of Ischemia,' J. Mol. Cell. Cardiol, 19(Supplement V) 45–53 (1987).

Wu et al., 'Ischemia–Modified Albumin, Free Fatty Acids, Whole Blood Choline, B–Type Natriuretic Peptide, Glycogen Phosphorylase BB, and Cardiac Troponin,' Cardiac Markers, Second Edition, edited by Alan H.B. Wu, Humana Press, Totowa, NJ (2003).

Abstract by Danne et al. entitled 'Whole Blood Choline and Plasma Choline Concentration for Early Risk–Stratification of Troponin I–negative Acute Coronary Syndromes,' published Nov. 9–12, 2003, at Scientific Sessions 2003 conference in Orlando, Florida.

Gillum et al., 'International diagnostic criteria for acute myocardial infarction and acute stroke,' Am. Heart J., 108(1):150–8 (1984).

Braunwald et al., 'Diagnosing and Managing Unstable Angina,' Circulation. 90:613–22 (1994).

Rude et al., 'Electrocardiographic and Clinical Criteria for Recognition of Acute Myocardial Infarction Based on Analysis of 3,697 Patients,' Am. J. Cardiol., 52:936–42 (1983).

Mair et al., Neue Laborparameter zur Diagnose und Überwachung akuter Myokardschäden, DG Klinishce Chemie Mitteilungen, 25:1–16 (1994).

Corr et al., 'Lysophosphoglycerides and Ventricular Fibrillation Early After Onset of Ischemia,' J. Mol. Cell Cardiol., 19(Supp. V):45–53 (1987).

Snyder et al., 'Lysophosphoglycerides in ischemic myocardium effluents and potentiation of their arrhythmogenic effects,' Am. J. Physiol., 241 (5):H700–7 (1981).

Akita et al. 'Electrophysiologic Effects of Intracellular Lysophosphoglycerides and Their Accumulation in Cardiac Lymph with Myocardial Ischemia in Dogs,' J. Clin. Invest., 78(1):271–80 (1986).

Takayama et al., 'A New Enzymatic Method for Determination of Serum Choline–Containing Phospholipids,' Clin. Chim. Acta, 79:93–8 (1977).

Brouwers et al., 'Quantitative analysis of phosphatidylcholine molecular species using HPLC and light scattering detection,' J. Lipid Res., 39(2):344–53 (1998).

Potter et al., 'Acetylcholine and Choline in Neuronal Tissue Measured by HPLC with Electrochemical Detection,' J. Neurochem., 41(1):188–94 (1983).

Myher et al., 'Molecular Species of Glycerophospholipids and Sphingomyelins of Human Erythrocytes: Improved Method of Analysis,' Lipids, 24(5):396–407 (1989).

Smal et al., 'Synthesis of a PAF Immunogen and Production of PAF–Specific Antibodies,' Lipids, 26(12):1130–5 (1991).

Pomfret et al., 'Measurement of Choline and Choline Metabolite Concentrations Using High–Pressure Liquid Chromatography and Gas Chromatography–Mass Spectrometry,' Analytical Biochemistry, 180:85–90 (1989).

Baldo et al., 'A Specific, Sensitive and High–Capacity Immunoassay for PAF,' Lipids, 26(12):1136–9 (1991).

Olsson et al., 'Molecular species analysis of phospholipids,' J. Chromatogr. B Biomed. Sci. Appl., 692(2):245–56 (1997).

Danne et al., 'Whole Blood Choline and Plasma Choline Concentration for Early Risk–Stratification of Troponin I–negative Acute Coronary Syndromes,' Circulation (Supplement IV), 108(17):p. IV–468, abstract 2150 (Oct. 28, 2003).

* cited by examiner

| total time period (0-35 h) | CCTD (> 22 μmol/l) | CK (> 100 U/l) | CK-MB (≥ 6% of CK) | Myo (> 90 ng/ml) | cTnI/T (cTnI > 1,5 μg/l) |
|---|---|---|---|---|---|
| sensitivity | 96.6 % | 57.1 % | 57.1 % | 60.7 % | 69.5 % |
| specificity | 92.8 % | 71.4 % | 100 % | 64.2 % | 92.8 % |
| positive predictive value | 96.6 % | 80.0 % | 100 % | 77.2 % | 94.7 % |
| negative predictive value | 92.8 % | 45.4 % | 53.8 % | 45.0 % | 52.0 % |
| diagnostic efficiency | 95.4 % | 61.9 % | 71.4 % | 61.9 % | 70.4 % |

Fig. 3: Diagnostic valency of choline, choline derivatives, and trimethyl ammonium derivatives (CCTD) compared with other infarction markers during total time period (0-35 h).

Number of samples (n) infarction group: CCTD n=30, CK/CK-MB/myoglobin (Myo) n=28, troponin I/T (cTnI/T) n=23; control group: all markers n=14

| early phase of AMI (0-6 h) | CCTD (> 22 μmol/l) | CK (> 100 U/l) | CK-MB (≥ 6% of CK) | Myo (> 90 ng/ml) | cTnI/T (cTnI > 1,5 μg/l) |
|---|---|---|---|---|---|
| sensitivity | 100 % | 37.5 % | 37.5 % | 62.5 % | 50.0 % |
| specificity | 92.8 % | 71.4 % | 100 % | 64.2 % | 92.8 % |
| positive predictive value | 94.7 % | 60.0 % | 100 % | 66.6 % | 87.5 % |
| negative predictive value | 100 % | 50.0 % | 58.3 % | 60.0 % | 65.0 % |
| diagnostic efficiency | 96.8 % | 53.3 % | 66.6 % | 63.3 % | 71.4 % |

Fig. 4: Diagnostic valency of choline, choline derivatives, and trimethyl ammonium derivatives (CCTD) compared with other infarction markers during the early phase of the AMI (0-6 h).

Number of samples (n) infarction group: CCTD n=18, CK/CK-MB/myoglobin (Myo) n=16, troponin I/T (cTnI/T) n=14; control group: all markers n=14

| early phase of AMI (0-3 h) | CCTD (> 22 μmol/l) | CK (> 100 U/l) | CK-MB (≥ 6% of CK) | Myo (> 90 ng/ml) | cTnI/T (cTnI > 1,5 μg/l) |
|---|---|---|---|---|---|
| sensitivity | 100 % | 12.5 % | 12.5 % | 50.0 % | 28.5 % |
| specificity | 92.8 % | 71.4 % | 100 % | 64.2 % | 92.8 % |
| positive predictive value | 88.8 % | 20.0 % | 100 % | 44.4 % | 66.6 % |
| negative predictive value | 100 % | 58.8 % | 66.6 % | 69.2 % | 72.2 % |
| diagnostic efficiency | 95.4 % | 50.0 % | 68.1 % | 59.0% | 71.4 % |

Fig. 5: Diagnostic valency of choline, choline derivatives, and trimethyl ammonium derivatives (CCTD) compared with other infarction markers during the early phase of the AMI (0-3 h).

Number of samples (n) infarction group: CCTD n=8, CK/CK-MB/myoglobin (Myo) n=8, troponin I/T (cTnI/T) n=7; control group: all markers n=14

| late phase of AMI (7-35 h) | CCTD (> 22 μmol/l) | CK (> 100 U/l) | CK-MB (≥ 6% of CK) | Myo (> 90 ng/ml) | cTnI/T (cTnI > 1,5 μg/l) |
|---|---|---|---|---|---|
| sensitivity | 91.6 % | 83.3 % | 83.3 % | 58.3 % | 100 % |
| specificity | 92.8 % | 71.4 % | 100 % | 64.2 % | 92.8 % |
| positive predictive value | 91.6 % | 71.4 % | 100 % | 58.3 % | 90.0 % |
| negative predictive value | 92.8 % | 83.3 % | 87.5 % | 64.2 % | 100 % |
| diagnostic efficiency | 92.3 % | 76.9 % | 92.3 % | 61.5 % | 69.6 % |

Fig. 6: Diagnostic valency of choline, choline derivatives, and trimethyl ammonium derivatives (CCTD) compared with other infarction markers during the late phase of the AMI (7-35 h).

Number of samples (n) infarction group: CCTD n=12, CK/CK-MB/myoglobin (Myo) n=12, troponin I/T (cTnI/T) n=9; control group: all markers n=14

IN-VITRO METHOD FOR DETECTING AND DIAGNOSING ACUTE CORONARY SYNDROMES

BACKGROUND OF THE INVENTION

The invention relates to an in vitro method of recognizing and diagnosing acute coronary syndroms, especially an acute myocardial infarction (AMI) in humans. Acute coronary syndromes comprise the syndroms of acute myocardial infarction and instable angina pectoris which are defined, respectively, by the WHO classification of AMI and the Braunwald classification of instable angina pectoris (Gillum R. F. et al. 1984, Am Hart J 108: 150–158; Braunwald E. et al. 1994, Circulation 90: 613–622). Acute coronary syndromes are a complex of diseases which occur frequently and often threaten life. An early, certain diagnosis and therapy may be decisive for the patient's survival. That is true particularly of an acute myocardial infarction in which case delayed proper diagnosis and late therapy may have serious consequences for the patient. There are such diagnostic measures of myocardial infarctions as the electrocardiogram and the determination of various laboratory markers. With a majority of patients, the sensitivity of the electrocardiogram and of the known laboratory markers is insufficient for diagnosis in the early phase of a myocardial infarction. As regards changes typical of an infarction reflected in the ECG (ST deflections), the sensitivity is 46% (Rude, R. E. et al. 1983, Am J Cardio 52: 936–942). The sensitivity of the laboratory markers creatine kinase (CK) activity, CK-MB activity, CK-MB mass, CK-MB isoforms, of myoglobin, and cardial troponins lies between 11–29% during the first two hours after the onset of pain (Mair, J. et al. Mitteilungen der Deutschen Gesellschaft für klinische Chemie 25: 1–6). The limited diagnostic usefulness of the known methods during the early phase of an acute myocardial infarction causes a number of clinical problems, such as the risk of erroneous diagnoses, carrying out treatments not indicated, and delaying life-saving therapies.

In the case of instable angina pectoris, patients at risk can be recognized with relative certainty by determining the cardial troponins. Due to the slow release kinetics, however, here too false negative findings are arrived at during the early phase. That is a problem because the prognosis of these patients may be about as bad as that of AMI patients and they need quick purposive antiischemic therapy. Considerable demand thus exists for methods which permit reliable, early recognition of acute coronary syndroms, particularly of an acute myocardial infarction.

SUMMARY OF THE INVENTION

It is, therefore, the object of the invention to indicate a method which allows early recognition of acute coronary syndroms, thus improving diagnosis and therapy of the stricken patients.

This object is met by a method comprising the features recited in claim 1. With the method according to the invention of recognizing and diagonising acute coronary syndroms, especially an acute myocardial infarction, the content of choline, choline and/or trimethyl ammonium derivatives selected from the group comprising phosphoryl choline, plasmalogens, and lysoplasmenyl choline is determined and evaluated in body fluids or component parts of the body withdrawn from a patient.

Choline, choline and/or trimethyl ammonium derivatives selected from the group comprising phosphoryl choline, plasmalogens, and lysoplasmenyl choline are molecules of the lipid meta-bolism and will be referred below in summary as "CCTD". CCTD have the following chemical formulae:

Choline: (formula 1)

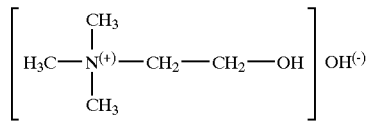

Choline derivatives: (formula 2)

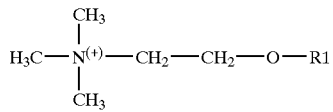

R1 = residue 1

Trimethyl ammonium derivatives: (formula 3)

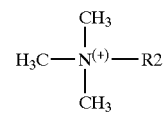

R2 = residue 2

R1 and R2 represent certain chemical substituents characterizing a group of substances comprising phosphoryl choline, plasmalogens, and lysoplasmenyl choline. Plasmalogens and lysoplasmenyl choline contain an alkenyl group in these molecule parts.

Formula 1 indicates that choline represents [2-hydroxyethyl] trimethyl ammonium together with its counter ion. Formula 2 gives the general chemical formula of choline derivatives, and formula 3 presents the general formula of trimethyl ammonium derivatives, such as phosphoryl choline, as well as of plasmalogens, such as plasmenyl choline and lysoplasmenyl. The negative charge may be in the same molecule or in a counter ion. The majority of the CCTD either are component parts of phospholipids which in turn represent elements of biological membranes or are closely related to the phospholipid metabolism. Cardiac muscle cells are particularly rich in plasmenyl cholines which represent choline-containing phospholipids having a characteristic alkenyl group in the molecule. Plasmenyl cholines, furthermore, are component parts of membranes of the mitochondria which account for a considerable part of the myocardial mass. Results obtained by the applicants show that the activation of various myocardial phospholipases in the early phase of the acute myocardial infarction as well as disturbances of the lipid metabolism upon severe myocardial ischemia bring about a distinct release of choline, choline derivatives, and of the chemically related trimethyl ammonium derivatives, such as phosphoryl choline, plasmalogens, or lysoplasmenyl choline, thereby provoking an increase in concentration of CCTD in certain body fluids and component parts of the body. The extent of participation of non-myocyte elements, including endothelium cells and smooth vascular muscle cells is not known.

The chemical relationship existing between choline, choline derivatives, and trimethyl ammonium derivatives selected from the group comprising phosphoryl choline, plasmalogens, and lysoplasmenyl choline as well as their similar behavior in pathophysiological processes, i. e. the very early release from the heart by ischemic membrane destruction are the reason for looking at them together, as CCTD.

Possible differences between the various CCTD stand back from the overwhelming common characteristic of very quick myocardial release in the event of acute coronary syndroms. This is all the more so considering the fact that the common characteristic mentioned is decisive for the essential feature of the method according to the invention in early diagnosis during the first few hours following the onset of pain.

Diagnostic utilization of the release of choline, choline derivatives, and trimethyl ammonium derivatives selected from the group comprising phosphoryl choline, plasmalogens, and lysoplasmenyl choline for recognition of acute coronary syndroms and acute myocardial infarction in humans has not been described as yet. The only thing known so far is that in experimental test arrangements in the early phase of myocardial ischemia a rise is observed of lysophosphoglycerides (e.g. lysophosphatidyl choline) in the myocardium and in venous as well as lymphatic effluvia (Corr, P. B. et al. 1987, J Mol Cell Cardiol 19: 34–53; Snyder, D. W. 1981, Am J Physiol 241: H700–H707; Akita, H. et al. 1986, J Clin Invest 78: 271–280). None of the publications applied a method of evaluating the content of choline, choline derivatives, and trimethyl ammonium derivatives selected from the group comprising phosphoryl choline, plasmalogens, and lysoplasmenyl choline in body fluids for diagnosing an acute coronary syndrom or an acute myocardial infarction in humans. The background of the publications cited, rather, is the observation that lysophosphatidyl choline apparently has proarrhythmic effects and that drugs having an anti-lysophosphatidyl choline effect possibly might be useful remedies.

The invention relates to a method of determining choline, choline and/or trimethyl ammonium derivatives, such as phosphoryl choline, plasmalogens, and lysoplasmenyl choline and/or certain reaction products for early diagnosis of acute coronary syndroms. A distinction must be made between non-inventive diacyl phosphatidyl cholines and inventive plasmenyl cholines. In the same manner, the non-inventive lysophosphatidyl cholines having an acyl group in the molecule must be distinguished from the inventive lysoplasmenyl cholines which have an alkenyl group in the molecule. Unspecific methods of determination which do not distinguish the substances according to the invention from other phospholipids or their components do not comprise the features of the method according to the invention which are essential for the early diagnosis of acute coronary syndroms. Therefore, they cannot be equated with the method.

Unspecific methods of determination of the whole group of plasma, serum, or whole blood phospholipids or lysophosphatidyl cholines, for instance, do not show the characteristics of the method according to the invention in the early diagnosis of acute coronary syndroms. These unspecific methods relating to phospholipids, as described in prior publications, essentially measure hepatic phospholipids in blood. And these hepatic phospholipids, as a matter of fact, do not contain the plasmenyl cholines and lysoplasmenyl cholines according to the invention. Instead they contain, quite predominantly, choline phospholipids without an alkenyl group, e.g. diacyl phosphatidyl choline. In view of the fact that the substances released by the heart into the blood in the event of acute coronary syndroms are not measured specifically by the non-inventive methods of determination, the methods in question do not comprise the features of the method according to the invention. In case of a myocardial infarction the non-inventive methods of determining phospholipids thus provide measurements either of no significant changes at all or even of reduced concentrations. This demonstrates that the methods in question do not detect the release of substances from the heart and a corresponding augmentation of the concentration thereof in blood. When determining the whole group of lysolecithins, for example, upon an acute myocardial infarction, often a reduction in concentration is measured because, in the unspecific acute-phase reaction, the formation of various acyl lysophosphatidyl cholines is reduced due to a decline in activity of the lecithin cholesterol acyl transferase (LCAT). Consequently measurements made with unspecific methods of determination of phospholipids often lead to contrary results and to conclusions which are not true of the method according to the invention.

The method according to the invention may be practiced with different analytical techniques, provided the substances according to the invention can be determined with sufficient specificity.

For instance, NMR spectroscopy may be applied upon preanalytical centrifugal ultrafiltration of the sample and removal of protein-bound diacyl phosphatidyl cholines which are not readily soluble. It is likewise possible to employ chromatographic, biochemical, or immunological methods of determination or other techniques. The analytical procedure may be conducted along the lines of methods of determination which have been published, for example, biochemical or enzymatic methods (Takayama, M. et al. 1977, Clin Chim Acta 79: 93–98), high performance liquid chromatography (HPLC) (Brouwers, J. F. H. et al. 1998, J Lipid Res 39: 344–353; Potter, P. et al. 1983, J Neurochem 41: 188–94) and gas chromatography and/or mass spectrometry (Myher, J. J. et al. 1989, Lipids 24: 396–407; Pomfret, A. et al. 1989, Anal Biochem 180:85) or immunological methods (Smal, M. A. et al. 1991, Lipids 26: 1130–1135; Baldo, B. A. et al. 1991, Lipids 26: 1136–1139). A survey of the analytics of phospholipids was published by Olsson (Olsson, N. U. et al.). We refer to these publications.

With biochemical methods according to the invention, for example, reagents (e.g. enzymes) are added to bring about chemical reactions or reaction products which then will permit detection and measurement of the whole group, a subgroup, or a subspecies of the CCTD (cf. examples of use).

With immunological methods according to the invention, for example, immunological reagents (antibodies) are used, usually together with other chemical and/or immunological reagents, to provoke reactions or yield reaction products which then will permit detection and measurement of the whole group, a subgroup, or a subspecies of the CCTD (cf. examples of use).

With chromatographic methods according to the invention, for example, upon preparation of the sample, a distribution of substances is effected between stationary and mobile phases so as to provide corresponding qualitative and quantitative data of CCTD (cf. examples of use).

It should be kept in mind with each analytical method of CCTD and their reaction products that some CCTD may form single layers, double layers, membranes, micelles, and/or vesicles and that these phenomena may be significant for the analyses.

Depending on the method of determination chosen, quantitative statements will be allowed to be made about certain individual groups or the entire group of substances analysed according to the invention. The prior publications mentioned are incorporated in the instant application by reference.

Certain activated phospholipases are significant in the cardial release of CCTD in the context of ischemic membrane destruction of cardiac muscle cells. These phospholipases cleave phospholipids so that, apart from CCTD, also simple reaction products result which, although not carrying a trimethyl ammonium group, still are released in the same way. Since these simple reaction products of CCTD are part of a common release mechanism the method can be carried out also by determining such simple reaction products. In addition to phospholipase $A_2$ which, among others, contributes to the release of the lysoplasmenyl choline mentioned, further important enzymes of this group are phospholipases C and D attacking the ester bond between the hydroxy group at the 3-sn-C atom of glycerol and phosphoryl choline (phospholipase C) or the bond between the phosphoryl group of the 1,2 substituted glycerol phosphate and the choline which is esterified with the phosphoryl group (phospholipase D). Reaction products resulting from the activity of these two phospholipases acting on the plasmalogens thus are 1-O-alk-1'-enyl-2 substituted glycerol (from phospholipase C) and 1-O-alk-1'-enyl-2 substituted glycerol phosphate (from phospholipase D), respectively. These reaction products are set free together with choline and phosphoryl choline, respectively, when the phospholipases mentioned exert their influence on plasmenyl choline. Consequently, the method according to the invention of an early diagnosis of acute coronary syndroms can be carried out by determining choline, choline and/or trimethyl ammonium derivatives selected from the group comprising phosphoryl choline, plasmalogens, and lysoplasmenyl choline, and/or the reaction products thereof selected from the group comprising 1-O-alk-1'-enyl-2 substituted glycerol and 1-O-alk-1'-enyl-2 substituted glycerol phosphate.

The increase of CCTD and their reaction products may be caused by the following further processes, in addition to the increased phospholipid activity: reduced decomposition and/or increased synthesis of CCTD and their reaction products (with corresponding changes of the responsible enzymes) and release from cellular compartments and membranes due to other factors (mechanical factors, cell swelling, and other phenomena of myocytic lesion).

BRIEF DESCRIPTION OF THE DRAWINGS

The invention will be explained with reference to the following embodiments.

FIG. 3 shows data of the diagnostic valencies of CCTD for diagnosis of an acute myocardial infarction over the entire period of examination;

FIG. 4 shows data of the diagnostic valencies of CCTD for diagnosis of an acute myocardial infarction in the early phase of the AMI (0 to 6 hours);

FIG. 5 shows data of the diagnostic valencies of CCTD for diagnosis of an acute myocardial infarction in the early phase of the AMI (0 to 3 hours); and FIG. 6 shows data of the diagnostic valencies of CCTD for diagnosis of an acute myocardial infarction in the late phase of the AMI (7 to 35 hours).

DESCRIPTION OF PREFERRED EMBODIMENTS

Figure 1:
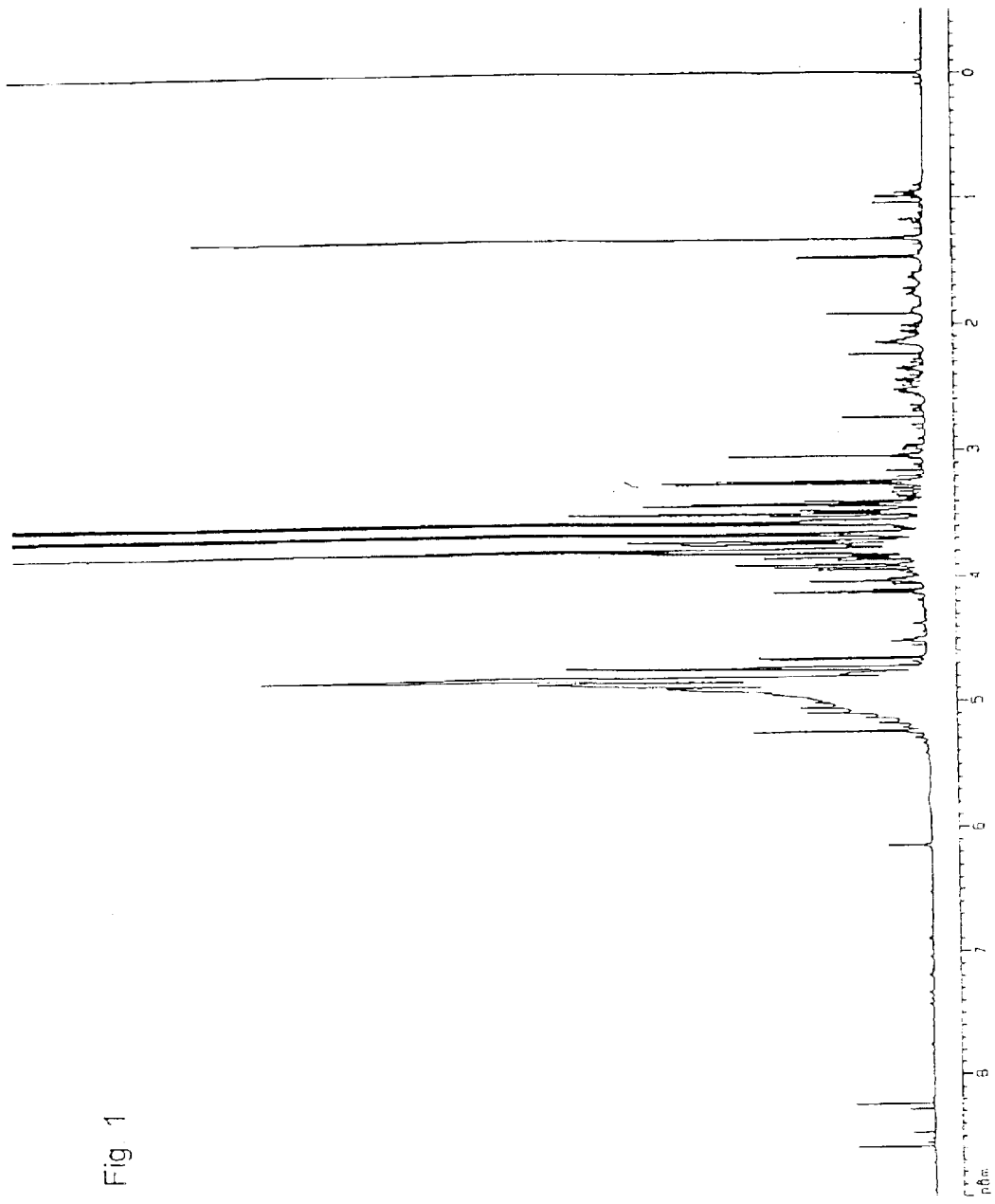
FIG. 1 shows a $^1$H-NMR spectrum of a patient's blood sample.

Selection and Withdrawal of a Suitable Sample of a Body Fluid

Withdrawal of a body fluid sample is required for carrying out the method. The diagnostic valency of the method depends on the body fluid chosen. The method may be carried out, for instance, by examining blood samples or processed blood samples, such as plasma, serum, or whole blood. Other body fluids, like urine also may be examined with the method, besides blood samples. To a certain extent, CCTD are filtered glomerularly and thus partly also appear in urine. As compared to blood sample examinations, however, a delay in time is to be expected for changes of concentration to take place, and that is a disadvantage of using urine. Besides, urine cannot always be obtained so easily and rapidly as blood, and this is another disadvantage. On the other hand, the use of urine samples is advantageous due to the fact that often greater sample quantities are available and that by measuring a concentration in a urine sample which was produced over a longer period of time, it is possible to detect pathophysiological processes over a longer period of time. However, for the reasons given, it is useful to utilize blood samples or processed blood samples for carrying out the method. It may make sense to effect the determination in other component parts of the body or other body fluids, for instance, tissue samples, lymph, or capillary blood. Further aspects should be taken in consideration when obtaining the sample. Any exogenous supply of greater amounts of choline, choline derivatives, or trimethyl ammonium derivatives prior to the sampling should be excluded. Moreover, the sample should be taken as soon as possible and perhaps be repeated periodically, for early recognition of acute coronary syndroms.

Determination of CCTD in a Body Fluid Sample

The diagnosing and evaluating method according to the invention is largely independent of the method of determination chosen as long as there is sufficient specificity for individual ones of the substances, a subgroup thereof, or all of the substances determined according to the invention. The substances determined according to the invention are choline, choline and/or trimethyl ammonium derivatives selected from the group comprising phosphoryl choline, plasmalogens, and lysoplasmenyl choline, as well as certain simple reaction products of the CCTD selected from the group comprising 1-O-alk-1'-enyl-2 substituted glycerol and 1-O-alk-1'-enyl-2 substituted glycerol phosphate. The $^1$H-NMR spectroscopy was selected as one embodiment and, being a primary measuring method, may be used also for validation. Other useful methods besides nuclear magnetic resonance methods (NMR) are biochemical, enzymatic, immunological, clinical-chemical, chromatographic, mass spectrometric, eletrochemical, photometric or other methods, provided cardially released CCTD (or their simple reaction products) are determined with high selectivity in patients suspected of suffering from acute coronary syndroms.

Clinical-chemical or other methods as well as quick tests for determining CCTD should be verified and validated as to their analytical quality. Wherever possible, nothing but methods proving to be widely equivalent or superior to $^1$H-NMR spectroscopy in terms of diagnostics should be drawn upon for diagnosing acute coronary syndroms. The explanations below of methods are given by way of example. In other words, chemicals, solutions, reagents, and devices which differ as to quality or quantity may be used as long as the results obtained remain comparable. In principle, it is sufficient to apply one valid measuring method of CCTD in one suitable body fluid to carry out the method according to the invention.

Embodiment: Determination of CCTD by $^1$H-NMR Spectroscopy

Preparing the sample:

withdrawing 10 ml of blood;

processing the blood sample in accordance with the sample material selected (serum, plasma, or whole blood);

centrifugal ultrafiltering of 4 ml of sample material by a 10 kD filter (e.g. Ultrafree-4B10; Millipore);

pipetting 600 μl ultra filtrate into a 5 mm NMR tube (e.g. 527-PP-7, Willmad, Buena, U.S.A.);

pipetting 100 μl of a 3,5-mM-$d_4$-TSP-$D_2O$ solution as concentration standard up to a sample volume of 700 μl (TSP=sodium salt of trimethyl silyl propionic acid);

measuring pH in the 5 mm NMR tube (e.g. 3 mm Minitrode, Hamilton) directly before or after the analysis.

High Resolution $^1$H-NMR Spectroscopy

The $^1$H-NMR spectra are prepared, for instance, by means of a 600 MHz spectrometer (e.g. Bruker AMX 600) under the conditions below:

single pulse mode water suppression with presaturation mode

30–90° rf impulse

5–15 s pulse repetition rate

64–128 scans per sample.

The $^1$H chemical shifts are referenced internally to $TSP_i$. The characterization of CH—, $CH_2$— and $CH_3$— groups as well as other proton-carrying groups of known substances is made on the basis of published $^1$H shift data. Additionally, proton resonances may be assigned in independent examinations by addition of purified substances. The concentration of individual substances is determined by determining the integrals of the corresponding proton resonances and the $TSP_i$ concentration standard, taking into consideration the respective proton number and the dilution factor. The quantitative evaluation of the spectra is performed according to the following formula.

$$C_M = F_d \frac{C_{TSP} A_M N_{TSP}}{A_{TSP} N_M} \quad \text{(formula 4)}$$

$C_M$ = concentration of metabolite $C_{TSP}$ = concentration of concentration standard $A_M$ = integral below peak of interest ($M$)

Figure 2:
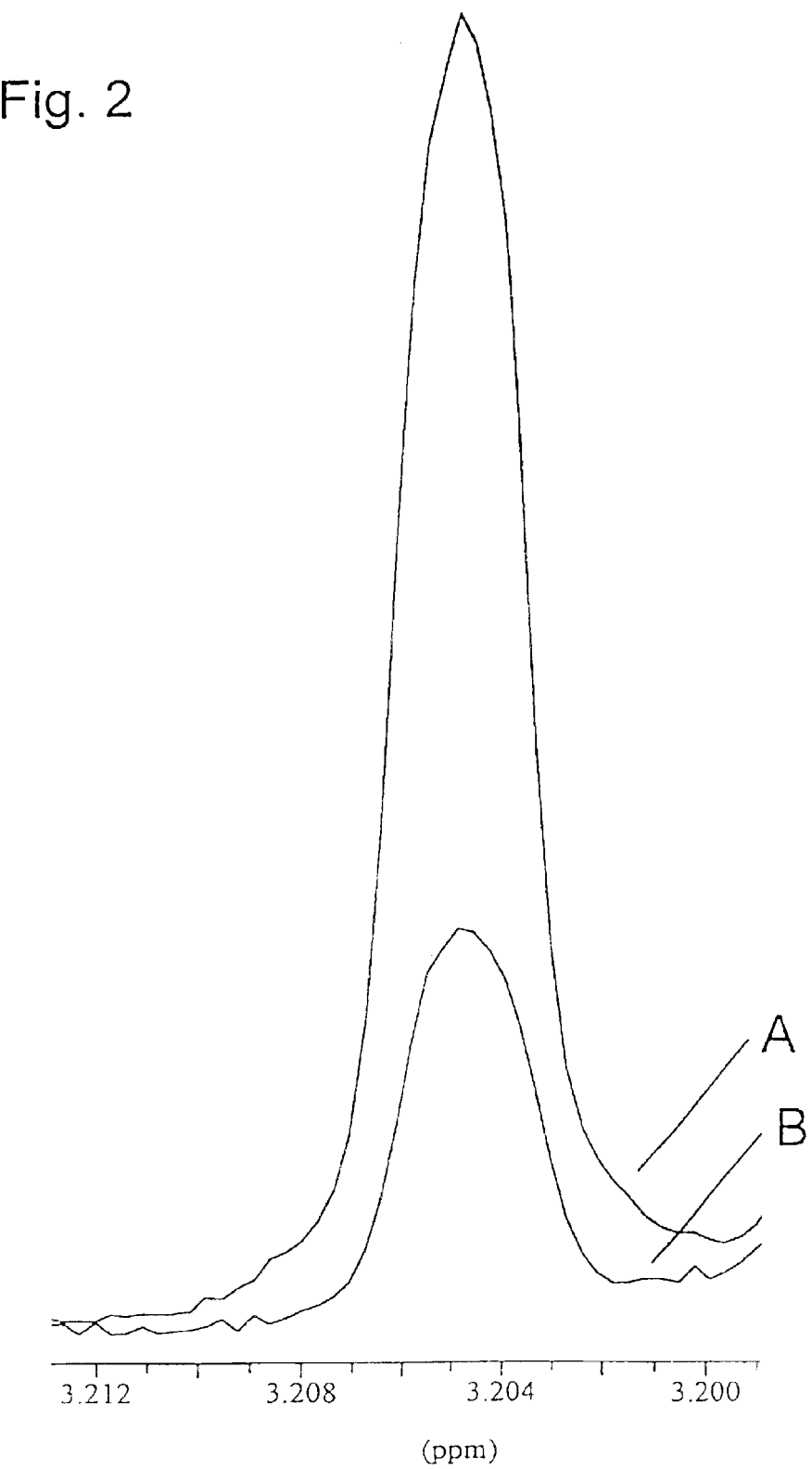
FIG. 2 shows enlarged cutouts of spectra analogous to FIG. 1 of an acute myocardial infarction patient (A) and a patient without acute myocardial infarction (B). Analogous areal elevations of $N^+(CH_3)_3$ singlets of CCTD are to be seen in acute myocardial infarction patients.

$A_{TSP}$ = intergal of concentration standard $F_d$ = dilution factor by addition of concentration standard $N_M$ = number of $M$ protons number of protons of concentration standard The method was validated by the applicants for determining low molecular substances and correlates at a correlation coefficient of r=0.998 with enzymatic methods. FIG. 1 illustrates a $^1$H-NMR spectrum of a patient. The typical singlet of the $N^+(CH_3)_3$ group of choline, choline derivatives, and trimethyl ammonium derivatives, as a rule, is detectable in a range between 2.5–4.5 ppm of the $^1$H-NMR spectra. Variations of the proton resonances are possible by various preanalytical influences, such as the pH, and theoretically such influences may lead to shifts, splittings and superpositioning so that they must be taken into account in the evaluation. It is useful to lay down precisely in separate test series the chemical shifts of the CCTD proton resonances for the conditions of investigation of the NMR analyses chosen. The $N^+(CH_3)_3$ singlet is especially well suited for quantification because it represents nine equivalent protons. An $N^+(CH_3)_3$ singlet with the typical evidence of an acute myocardial infarction is illustrated in FIG. 2. The concentration of CCTD is determined according to the method specified above. NMR spectroscopy offers the possibility of determining the total group, a subgroup, or a subspecies of the CCTD, e.g. by varying the analytics and evaluation, while immunological or biochemical methods according to the invention often serve to determine a subgroup or subspecies of CCTD. Further embodiments of the method according to the invention may be realized by using other CCTD determination methods than NMR spectroscopy. With biochemical methods according to the invention, for instance, the addition of reagents (e.g. enzymes) causes chemical reactions or yields reaction products which then make it possible to detect and measure the whole group, a subgroup, or a subspecies of the CCTD. Such an embodiment of the method according to the invention may be carried out, for example, by modifying the method published by Takayama (Takayama, M. et al. 1977, Clin Chim Acta 79: 93–98). Choline is determined by way of oxidation of choline by means of cholinoxidase, the reaction products obtained being betaine and hydrogen peroxide ($H_2O_2$). The formation of hydrogen peroxide ($H_2O_2$) is demonstrated by a color reaction, e.g. by coupling of 4-amino antiporine and phenol in the presence of a peroxidase, and the concentration is found out by measuring the absorption at 500 nm in a calibrated UV spectrophotometer against the blank sample.

A similar method which, however, is non-inventive, likewise may be used for determining the entire group of choline phospholipids. When using an unspecific phospholipase D without a prior separating process, that method will not comprise the essential features of the invention because also the large group of non-inventive diacyl phospholipids are included in the measurement. The specificity of the phospholipase used in the analysis or the provision of a prior separating process decides on the specificity or the kind of substances analyzed. If an unspecific phospholipase D is employed which is not preceded by an additional separating process the whole unspecific group of choline phospholipids are measured so that the essential features of the invention are not fulfilled. If a specific phospholipase D or a specific lysophospholipase D is used having substrate specificity for the plasmenyl cholines and/or lysoplasmenyl cholines according to the invention then an embodiment of the method according to the invention becomes possible because substances according to the invention in that case will be measured specifically. Utilization of these plasmalogen-specific phospholipases or lysophospholipases for the analysis of CCTD has not been published up to now, in particular not as used according to the invention for diagnosing acute coronary syndroms If the sample is especially prepared (e.g. by chromatographic separation processes, filtration, or methods of enrichment) before the use of phospholipases so that non-inventive phospholipids, especially diacyl phospholipids originating from the liver were removed the substrate specificity of the phospholipase or lysophospholipase, of course, no longer plays such a dominant role, and the specificity of the method is decided by the preceding separating processes. Leaving out phospholipases or lysophospholipases altogether results in the determination of choline in the course of the analysis, as indicated above, and that again means practicing the method of the invention as applied for the diagnosis of acute coronary syndroms. Choline also may be determined by a simple precipitation reaction and subsequent photometry. With these simple embodiments, the specificity of the method with respect to the substances according to the invention should be verified thoroughly. With biochemical determination according to the invention of choline or other CCTD in whole blood, haemolysis of the erythrocytes e.g. by saponins may be effected prior to the quantitative determination.

With immunological methods according to the invention, for example, the use of immunological reagents (e.g. antibodies), generally in conjunction with other chemical and/or immunological reagents, induces reactions or provides reaction products which then permit detection and measurement of the whole group, a subgroup or a subspecies of CCTD. These immunological methods according to the invention may be carried out in practice along the lines of the method published by Smal and Baldo (Smal, M. A. et al. 1991, Lipids 26: 1130–1135; Baldo, B. A. et al. 1991, Lipids 26: 1136–1139). Reference is made to these publications. In a first step a CCTD immunogen is produced so as to develop an immunological testing method according to the invention. Synthesized or highly purified CCTD are transformed into stable CCTD analogues and bound to proteins (e.g. methylated bovine serum albumin). Thereupon animals (e.g. rabbits or sheep) are immunized with the CCTD protein conjugate, and the anti-CCTD antibodies formed are isolated and purified, e.g. by means of affinity chromatography. The specificity of the antibodies for CCTD and/or a subgroup or subspecies of CCTD should be verified respectively. Finally, the anti-CCTD antibodies are ready for application with various immunological techniques to perform quantitative diagnostics.

When a radioimmunoassay is selected, radioactively labeled antigens, e.g. $^{125}$I-CCTD compete with the antigen of the sample (CCTD of the sample) for a short of anti-CCTD antibodies in the test preparation. A quantitative relationship exists between the displacement of radioactively labeled CCTD from anti-CCTD antibodies and the CCTD concentration in the sample and, therefore, the concentration can be determined once a standard curve has been established and upon precipitation of radioactive CCTD which are bound to antibodies, for example.

Applying a similar principle, a CCTD chemoluminescence immunoassay (CCTD-CELIA) may be performed to determine CCTD. CCTD and Luminol-labeled antigen compete for a limited quantity of solid-phase bound antibodies. The measurable light signal is inversely proportional to the CCTD concentration in the patient sample.

Immunological determination of CCTD, furthermore, may be achieved by a CCTD fluorescence-polarization immunoassay. With this assay a defined quantity of fluorophor-labeled CCTD compete with the CCTD in the sample for a short of corresponding anti-CCTD antibodies. The influence on the fluorophor-labeled CCTD following antibody binding is recorded. Fluorescence polarization is used for measuring; it measures the angular change of the polarized fluorescence radiation emitted by the fluorophor upon excitation. During the period between absorption and emission of radiation, the fluorophor-labeled CCTD which are bound to antibodies can rotate only a little, whereas they can do so well when free. The polarization is strong (small angular variation of the emitted radiation) when the CCTD concentration is low, while it is weak (great angular variation) at high CCTD concentrations.

The immunological determination of CCTD according to the invention also may be carried out by way of a sandwich assay if the CCTD or the subgroups or subspecies of CCTD to be determined comprise at least two different epitopes or can be transformed by a specific reaction into a substance having at least two different epitopes. Under these circumstances a CCTD enzyme linked immunoabsorbent assay (CCTD-ELISA) is feasible. The anti-CCTD antibody is coupled to a solid phase, such as a well on a microtiter plate, magnetic particles, plastic beads, or a tube wall. Upon addition of the suitably prepared sample, the CCTD of the sample bind to the antibody. The amount of CCTD antigen thus bound is determined by adding a labeled second antibody which will bind to the CCTD antigen, thus forming a sandwich. The higher the concentration of bound CCTD, the greater the quantity of CCTD antigen bound in the sandwich, for instance by an enzyme labeled second antibody. A linear relationship exists between the CCTD concentration and the enzyme activity for a certain range of concentration of CCTD.

A similar method of determination according to the invention is the microbead enzymimmunoassay of CCTD (CCTD-MEIA) wherein the anti-CCTD antibody is bound to microbeads. In a first step the sample is incubated with the antibody microbeads, thereupon an alkaline phosphatase (AP)-labeled second antibody is added. As a result, a sandwich is formed on the microbead. In a subsequent step, part of the reaction mixture is pipetted on to a fiber glass matrix characterized by high affinity to the microbead so that it binds the latter. After washing of the fiber glass matrix with substrate solution and removal of non-bound AP-labeled second antibody, the AP which is bound to the microbead as a sandwich is able to cleave off the phosphate group from the methylumbelliferryl phosphate substrate, for example. The fluorescence of the resulting methylumbelliferon is measured in incident light at 448 nm. The sandwich techniques are not suited for small molecules which possess only one epitope, they are useful only with CCTD which are selected from the group having at least two epitopes or CCTD which can be transformed by a specific chemical reaction into analogous molecules having at least two epitopes.

Other variants and specifications of immunological CCTD determinations are conceivable, including direct immunological antigen determinations, determinations in the form of soluble immune complexes, indirect antigen determinations, further determinations of antigens and antibodies by labelling one of the reaction partners, ligand binding assays, and other heterogeneous and homogeneous immunoassays. In the context of an immunological CCTD determination, separation techniques, like adsorption, precipitation, immune precipitation, and/or the solid phase principle are applicable just like different labelling techniques, such as radioactive labelling (e.g. $^{1251}$I), enzymatic labelling (e.g. alkaline phosphatase, horseradish peroxidase, glucose-6-phosphate dehydrogenase), fluorescence labelling or luminescence labelling (e.g. chemiluminescence, bioluminescence). The decisive criterion is the specific determination of CCTD or a subgroup or subspecies of CCTD or of the reaction products mentioned and the application thereof for diagnosing acute coronary syndroms.

In the case of chromatographic methods according to the invention for determining CCTD, for instance, a sample is prepared and substance separation caused by partitioning between a stationary phase and a mobile phase to provide corresponding qualitative and quantitative findings in respect of CCTD. The determination according to the invention of CCTD may be effected along the lines of the Brouwers method (Brouwers, J. F. H. et al. 1998, J Lipid Res 39: 344–353). Following the preparation of the sample and lipid extraction, first phosphatidyl cholines are separated from other lipids. That may be accomplished by high resolution liquid chromatography (HPLC), e.g. in the form of normal phase HPLC (NP-HPLC). The respective separation and collection of the eluates is followed by reverse phase chromatography (RP-HPLC), employing as solvents, for example, acetonitrile, methanol, and triethylamine. A suitable detection system is light scattering detection. Calibration curves may be established on the basis of examinations of standard solutions in combination with determinations of phosphorus, whereby a quantitative determination of CCTD is rendered possible, in particular also the determination of certain CCTD subspecies.

When comparing them with the NMR method, the chromatographic and immunological methods of determination have the advantage of specifically determining a certain plasmenyl choline sub-species with a defined alkenyl group at the sn-1 position and a certain acyl group at the sn-2 position, or of distinguishing the same from other similar molecules, thereby offering improved organ specificity of the method.

It is obvious to those skilled in the art that methods of determination similar to the ones described above may be used just as well for determining CCTD reaction products in accordance with the invention.

Especially well suited for a determination according to the invention of CCTD subspecies are those molecules with which the number of false positive test results remains low when diagnosing acute coronary syndroms. Among others, the subspecies listed below, including their reaction products are significant and may be determined either individually or in any desired combination to perform the method according to the invention: 16:0–20:3 plasmenyl choline, 16:0–18:3 plasmenyl choline, 17:0–18:2 plasmenyl choline, 15:0–18:2 plasmenyl choline, 17:0–18:1 plasmenyl choline, 17:0–18:3 plasmenyl choline, 16:0–17:1 plasmenyl choline, 14:0–18:2 plasmenyl choline, 15:0–18:1 plasmenyl choline, 16:0 lysoplasmenyl choline, 17:0 lysoplasmenyl choline, 15:0 lysoplasmenyl choline, 14:0 lysoplasmenyl choline, and the reaction products 16:0(alk-1-enyl)-20:3 glycerol, 16:0(alk-1-enyl)-18:3 glycerol, 17:0(alk-1-enyl)-18:2 glycerol, 15:0(alk-1-enyl)-18:2 glycerol, 17:0(alk-1-enyl)-18:1 glycerol, 17:0(alk-1-enyl)-18:3 glycerol, 16:0(alk-1-enyl)-17:1 glycerol, 14:0(alk-1-enyl)-18:2 glycerol, 15:0(alk-1-enyl)-18:1 glycerol, 16:0(alk-1-enyl)-20:3 glycerol phosphate, 16:0(alk-1-enyl)-18:3 glycerol phosphate, 17:0(alk-1-enyl)-18:2 glycerol phosphate, 15:0(alk-1-enyl)-18:2 glycerol phosphate, 17:0(alk-1-enyl)-18:1 glycerol phosphate, 17:0(alk-1-enyl)-18:3 glycerol phosphate, 16:0(alk-1-enyl)-17:1 glycerol phosphate, 14:0(alk-1-enyl)-18:2 glycerol phosphate, and 15:0(alk-1-enyl)-18:1 glycerol phosphate. Further CCTD subspecies and reaction products may be selected for the method according to the invention, provided the features of the invention are fulfilled with their determination.

When the method is performed by applying NMR spectroscopy, the analysis may be extended to include other molecule portions in addition to analyzing $N^+(CH_3)_3$ singlets. Moreover, the NMR spectroscopy may be practiced as one-, two-, or multidimensional NMR spectroscopy or by other NMR spectroscopic examining techniques, among others also coupled with chromatographic methods (for example, as LC-NMR).

It is common to all the different possible methods and techniques of determination according to the invention that the specificity of the method for CCTD is high so that the essential features of the invention of an early diagnosis of acute coronary syndroms are fulfilled. Certain steps in the preparation of the sample may be important for selectively determining cardially released CCTD by a method according to the invention. With the methods described, for instance, the preanalytical ultrafiltration reduces the amount of non-inventive, protein-bound, hepatic diacyl choline phospholipids or eliminates them altogether, depending on the filter used. On the other hand, the free, soluble fraction of cardially released CCTD, including the plasmalogens is measured in the ultrafiltrate. Other methodical purification and/or extraction steps or biochemical modifications may be applied and will yield comparable results. Moreover, the method according to the invention may be carried out in a way such that one or several or all of the molecular subspecies of cardially released CCTD or their reaction products are analyzed.

In addition to the determination of CCTD, the $^1$H-NMR spectroscopy offers the possibility of determining further metabolites in the same investigative run. These may be creatine (singlet at 3.93 ppm) and dimethylamine (singlet at 2.727 ppm), for instance, which likewise are significant for infarction diagnostics. Combining the evaluation of a plurality of metabolites in one investigative run (e.g. CCTD, creatine, and dimethylamine) is here referred to as pattern recognition. The strength of diagnostic statements which the method of an early recognition of acute coronary syndroms permits is improved by an evaluation in the pattern recognition mode as compared to the isolated determination of the concentration of CCTD.

Evaluation of the CCTD Measurement Results

A limit value is taken into consideration when evaluating the results of the measurements made. The limit value depends on the body fluid examined and on the method of determination chosen and must be laid down upon corresponding examinations. An acute myocardial infarction is indicated if the measured value obtained for CCTD turns out to be higher than the limit value. If the measured value is lower than the limit value an acute myocardial infraction practically may be excluded. The same applies to diagnosing instable angina pectoris in which case the limit values must be set by examining a sufficiently great number of patients and in consideration of the diagnostic questions to be answered. In the case of our methods of determining the concentration of CCTD the limit value lies between 15–40 $\mu$mol/l depending on the evaluation mode. The clinical data shown relate to an evaluation where the limit value was 22 $\mu$mol/l. As already stated, the limit value must be fixed specifically in correspondence with the analytical method selected, the evaluation mode, and the respective questions. For immunological and chromatographic determinations of CCTD subspecies, for instance, the limit value may be located in a different measuring range altogether, such as the nanomolar or subnanomolar ranges. With the $^1$H-NMR spectroscopy, an evaluation in the pattern recognition mode (e.g. additional determination of creatine and dimethylamine) may be performed besides the determination of the concentration of CCTD in isolation. An increase in CCTD or creatine, at simultaneous normal concentrations of dimethylamine, was drawn upon for an AMI diagnosis when the evaluation was done in the pattern recognition mode.

Findings from Patients

A total of twenty patients and test persons (8 f, 12 m) aged 22–68 years were examined, in part periodically, with a total of 44 samples. Further samples were studied, based on special questions. 10 patients had suffered an acute myocardial infarction (4 anterior wall, 6 posterior wall infarctions). The samples were taken at different intervals 1 h–35 h after the onset of pain. 60% of samples were obtained during the first six hours after the onset of pain. All patients with AMI were subjected to coronary angiography (9 patients acute, and 1 patient during progress). 9 patients with AMI received reperfusion therapy, i.e. thrombolysis, primary percutaneous transluminal coronary angioplasty (PTCA), thrombolysis with rescue PTCA, or an acute aortocoronary vein bypass operation (ACVB-OP). One female patient showed spontaneous recanalization in the infarcted vessel during the acutely applied coronary angiography and a residual thrombus with good post-stenotic flow so that a primary PTCA was dispensed with. In the control group, one patient suffering from severe acute thoracic pain was subjected to acute coronary angiography as a result of which a coronary heart disease could be excluded. There were different diseases in the control group, such as instable angina pectoris, stable angina pectoris, skeletal muscle trauma, myopathy, condition following lung embolism, pleuritis, and renal insufficiency. The patients with acute myocardial infarctions displayed a typical pattern of complications, for instance, left ventricular insufficiency and arrhythmia. One patient with an anterior wall infarction arrived in cardiogenic shock condition requiring reanimation, and he survived it upon thrombolysis, acute PTCA with a stent implant, and intraaortal balloon pump (IABP) implantation.

The Concentration of CCTD was Determined in all the Samples.

The limit value which had been set was taken into account when evaluating the measured results of CCTD. As already explained, measured values above the limit value indicate an acute myocardial infarction. No acute myocardial infarction is given if the measured values lie below the limit value. The diagnostic valency was determined with reference to the particular sample, in other words the result of an individual measurement was assessed regardless of results of earlier or later measurements of the patient. The CCTD were found to be above the limit value in 29 of the 30 infarction samples. Inversely, with the exception of one sample, the CCTD of all patients without an infarction were less than the limit value. FIG. 3 shows the data of the diagnostic valency of CCTD for the diagnosis of an acute myocardial infarction over the entire period of time from 0–35 h. It follows from FIG. 3 that at 96.6% CCTD have the highest sensitivity and at 95.4% they have the highest diagnostic efficiency in comparison with all the other infarction markers. The high diagnostic valency of CCTD is noteworthy also because many patients were examined who were difficult to diagnose, i.e. patients with microinfarctions (4 out of 10 patients), patients during the first hours of the infarction, and patients with skeletal muscle trauma.

In terms of their diagnostic valency, CCTD were superior to the conventional infarction markers, especially so during the early phase of the AMI. During the time period from 0 to 6 hours after the beginning of pain, all the infarction patients were CCTD positive, while only 37.5% of the patient samples had a pathological CK or CK-MB (see FIG. 4). In correspondence with its high release rate, myoglobin had the second highest sensitivity at 62.5% but, as is well known, it is not myocard-specific. During the first 6 hours only 50% of the samples of the patients with AMI showed a pathological troponin I/T concentration.

The advantages of CCTD are evidenced even more strikingly if one looks merely at the patient samples of hours 0–3 after the onset of pain (FIG. 5). While conventional infarction markers hardly are diagnostically meaningful during the first three hours after the beginning of pain, their diagnostic efficiency being no better than between 50% and 71%, CCTD recognized all the infarction samples which were examined during the first three hours after the beginning of pain. Further results of investigations made by the applicants confirm the rapid release of CCTD with acute coronary syndroms and their great diagnostic value in the early phase after the symptoms begin to appear. During the late phase of the AMI a minor reduction is recorded in the sensitivity of CCTD.

FIG. 6 illustrates the diagnostic valency of CCTD in the late phase of the AMI. The sensitivity of CCTD was 91.6% in the late phase of the AMI. A false negative test result was obtained from one sample.

An increase in CCTD was 92.8% specific for an acute myocardial infarction. In one sample an increase of CCTD was observed although there was no acute myocardial infarction.

Evaluation of $^1$H-NMR spectra in the pattern recognition mode (simultaneous determination of CCTD, their reaction products, creatine, and dimethylamine, as well as any desired suitable combinations thereof) resulted in improved diagnostic certainty of the method so that every myocardial infarction could be diagnosed or excluded, respectively, with 100% sensitivity and 100% specificity at any point in time, in the examinations completed so far.

As is well known, the prognosis of patients suffering from instable angina pectoris is worse if increased values of cardial troponins are discovered in the progress thereof (Ohmann, E. M. 1996, N Engl J Med 335: 1333–41). It is assumed that these patients not only go through myocardial ischemia but also suffer myocardial micronecroses so that it cannot be excluded that, in future, these patients will be classified under microinfarctions when the AMI may be judged according to new classifications. It is essential that these patients be identified quickly because, as rule, they should be treated without delay and must undergo emergency angiography, if necessary. The examinations b the applicants have revealed that patients with angina pectoris and an uncomplicated course of the disease do not have elevated levels of CCTD, whereas the CCTD values are higher for all those patients with myocardial micronecroses. It follows from the results gathered thus far that all patients with acute coronary syndroms who are CCTD positive develop higher troponin values in the course of events. For patients with micronecroses, the serial examinations likewise showed that the results for CCTD were positive several hours sooner than for troponin I or troponin T. Moreover, it must be assumed that the method will be helpful also in diagnosing severe myocardial ischemias, e.g. upon catheter interventions in the coronaries or in case of diseases with an involvement of the myocardium, such as myocardites. The results obtained by the applicants prove that the method is precious both with the acute myocardial infarction and also with instable angina pectoris, in other words quite generally when there is suspicion of an acute coronary syndrom.

In consideration of the fact that CCTD, once released, continue to be metabolized or modified by various biochemical processes, choline, choline derivatives, and trimethyl ammonium derivatives are not the only substances produced but an increased number of reaction products of CCTD result as well. These reaction products may represent fractions or certain metabolites of CCTD. As is known with CK isoenzyms, for example, the simultaneous determination of such reaction products of infarction markers can be advantageous for diagnostic purposes. There were indications in the examinations carried out by the applicants that such reaction products of CCTD were produced in some of the patients who suffered from infarctions. The origination of those reaction products is due, among others, to the enhanced activity of certain phospholipases. In addition to phospholipase A2 which, among others, contributes to the release of the so-called lysoplasmenyl choline, other important enzymes of this group are the phospholipases C and D, as mentioned above. Reaction products of the activity of these two phospholipases in acting on the plasmalogens are, for example, 1-O-alk-1'-enyl-2 substituted glycerol (from phospholipase C) and 1-O-alk-1'-enyl-2 substituted glycerol phosphate (from phospholipase D). Enhanced formation of these reaction products occurs along with choline and phosphoryl choline, respectively, when the phospholipases mentioned act on plasmenyl choline during myocardial ischemia. The method, therefore, can be implemented also by detecting the simple reaction products named of CCTD, in combination with CCTD determinations, if so desired.

Time Course of the Release of CCTD Upon an Acute Myocardial Infarction

The analysis of all measurement values available for CCTD (excluding one non-representative sample) proved that the CCTD become positive within 60 minutes from the beginning of pain and obviously have biphase release kinetics, with an early maximum after 2–3 hours and a second maximum after 5–6 hours. A comparison with other infarction markers revealed that, in correspondence with the low molecular weight, the release of CCTD is much quicker than the release of the markers known so far. That explains the high diagnostic valency attained during the early phase.

Further examinations undertaken by the applicants on more than 100 patients who complained of chest pains confirmed the superiority of the method according to the invention over use of conventional markers as well as the characteristics according to the invention for the early diagnosis of acute coronary syndroms.

The method of recognizing the acute myocardial infarction and severe forms of instable angina pectoris by way of determining and evaluating the contents of choline, choline and/or trimethyl ammonium derivatives selected from the group comprising phosphoryl choline, plasmalogens, and lysoplasmenyl choline, and their simple reaction products in body fluids appears to be superior to all non-invasive methods so far introduced, including the determination of known biochemical markers for diagnosing acute coronary syndroms. Not only the acute myocardial infarction but also severe forms of instable angina pectoris with myocytic necroses showing elevated troponin values in the course of events are recognized early on by the method. The results prove that the method is useful both with the acute myocardial infarction and with instable angina pectoris, i.e. quite generally when suspicion exists of an acute coronary syndrom. The special value of the invention is underlined by the fact that it will be possible for the first time with the in vitro method of the invention to offer an early safe diagnosis or a diagnosis of exclusion to patients with acute coronary syndroms and acute myocardial infarctions, early meaning within the first three hours after pain has set in. That is not possible with a comparably high degree of certainty with any in vitro method published. The American Heart Association and the American College of Cardiology have stated that there is ". . . a clear need for better methods of prompt identification of patients experiencing a true acute MI as accurately and as soon as possible" (Ryan, T. J. et al. ACC/AHA Guidelines for the Management of Patients with Acute Myocardial Infarction, 1996 J Am Coll Cardiol 28: 1328–1428, p. 1340). Such a method is not on hand at the present time. The method presented by the invention meets exactly the required characteristics, as follows from the data at the applicants' disposal.

The method relates to the diagnosis of the clearly defined symptoms of acute coronary syndroms, comprising instable angina pectoris and acute myocardial infarction which may manifest itself as a Q-wave or non-Q-wave myocardial infarction. Examinations relating to other syndroms, such as brain infarctions which differ in many respects as regards their pathomorphology and pathobiochemistry do not permit conclusions of analogy to be drawn with respect to the method according to the invention.

The method according to the invention for early diagnosis of acute coronary syndroms can be carried out with different techniques or procedures of determination, all the more so as equivalent measurement results of certain substances often can be obtained with different measuring methods, many descriptions of which are to be found in publications, as far as CCTD are concerned. In addition to the selection of one suitable measuring technique, the method comprises the selection of one suitable body fluid, preparation of the sample in accordance with the procedure and technique chosen, specific measurement of the content of CCTD and/or their reaction products selected from the group comprising 1-O-alk-1'-enyl-2 substituted glycerol and 1-O-alk-1'-enyl-2 substituted glycerol phosphate, as well as proper evaluation in accordance with the method for diagnosing patients with acute coronary syndroms. It is possible to apply the method also in the examination of other component parts of the body, e.g. tissue samples since CCTD are released into various other body fluids and component parts of the body. Yet the diagnostic valency possibly may be reduced in comparison with the embodiment specified. The method, furthermore, can be practiced by determining reaction products because the release of CCTD is accompanied by a great many reaction products of CCTD, selected from the group which comprises 1-O-alk-1'-enyl-2 substituted glycerol and 1-O-alk-1'-enyl-2 substituted glycerol phosphate. Moreover, the method can be carried out such that semi-quantitative or qualitative statements are made, in other words such that, for instance, quick tests in respect of CCTD merely indicate by a color reaction whether or not a myocardial infarction exists. The method may be executed in such a way that conditions or processes are watched or induced which are determined by the content of CCTD or CCTD reaction products. The method not only permits recognition of acute coronary syndroms but also offers the prospect of additional diagnostic information, such as the size of the infarction, prognosis, control of therapy, and prediction of certain complications, risks, and of the clinical progress. The special value of the method according to the invention is highlighted by its diagnostic properties which have long been demanded for in vitro methods of early diagnostics of acute coronary syndroms by international expert committees, like the American Heart Association and the American College of Cardiology.

On the whole, the method is intended to help overcome the considerable problems confronting present day early diagnostics of acute coronary syndroms and to improve the diagnosis and therapy of diseased patients.

The features disclosed in the specification above, in the claims and drawing may be essential to the implementation of the invention, both individually and in any desired combination.

What is claimed is:

1. An in vitro method of recognizing and diagnosing acute coronary syndromes, generally when there is suspicion of an acute coronary syndrome, namely an acute myocardial infarction and/or severe forms of unstable angina pectoris involving myocardial micronecrosis, characterized by determining the content of choline, choline and/or trimethyl ammonium derivatives selected from the group comprising phosphoryl choline, plasmalogens, and lysoplasmenyl choline (CCTD) in body fluids or component parts of the body wherein an increase in CCTD causes the diagnosis of acute coronary syndromes, namely an acute myocardial infarction and/or severe forms of unstable angina pectoris involving myocardial micronecrosis.

2. The in vitro method as claimed in claim 1, characterized in that the content of choline, choline and/or trimethyl ammonium derivatives selected from the group comprising phosphoryl choline, plasmalogens, and lysoplasmenyl choline (CCTD) is evaluated taking into account a limit value.

3. An in vitro method of recognizing and diagnosing acute coronary syndromes, generally when there is suspicion of an acute coronary syndrome, namely an acute myocardial infarction and/or severe forms of unstable angina pectoris involving myocardial micronecrosis, characterized by determining the content of reaction products of choline, choline and/or trimethyl ammonium derivatives selected from the group comprising phosphoryl choline, plasmalogens, and lysoplasmenyl choline (CCTD) in body fluids or component parts of the body, the reaction products being selected from the group comprising 1-O-alk-1'-enyl-2 substituted glycerol and 1-O-alk-1'-enyl-2 substituted glycerol phosphate, wherein an increase in reaction products of CCTD causes the diagnosis of acute coronary syndromes, namely an acute myocardial infarction and/or severe forms of unstable angina pectoris involving myocardial micronecrosis.

4. An in vitro method of recognizing and diagnosing acute coronary syndromes, generally when there is suspicion of an acute coronary syndrome, namely an acute myocardial infarction and/or severe forms of unstable angina pectoris involving myocardial micronecrosis, characterized by watching a condition or process in body fluids or component parts of the body which condition or process is determined by the content of choline, choline and/or trimethyl ammonium derivatives selected from the group comprising phosphoryl choline, plasmalogens, and lysoplasmenyl choline (CCTD), and/or the reaction products thereof selected from the group comprising 1-O-alk-1'-enyl-2 substituted glycerol and 1-O-alk-1'-enyl-2 substituted glycerol phosphate, wherein an increase in CCTD and/or reaction products of CCTD causes the diagnosis of acute coronary syndromes, namely an acute myocardial infarction and/or severe forms of unstable angina pectoris involving myocardial micronecrosis.

5. An in vitro method of recognizing and diagnosing acute coronary syndromes, generally when there is suspicion of an acute coronary syndrome, namely an acute myocardial infarction and/or severe forms of unstable angina pectoris involving myocardial micronecrosis, characterized in that quantitative, semiquantitative, or qualitative observations are made which are determined by the content of choline, choline and/or trimethyl ammonium derivatives selected from the group comprising phosphoryl choline, plasmalogens, and lysoplasmenyl choline (CCTD), and/or the reaction products thereof selected from the group comprising 1-O-alk-1'-enyl-2 substituted glycerol and 1-O-alk-1'-enyl-2 substituted glycerol phosphate in body fluids or component parts of the body, wherein an increase in CCTD and/or reaction products of CCTD causes the diagnosis of acute coronary syndromes, namely an acute myocardial infarction and/or severe forms of unstable angina pectoris involving myocardial micronecrosis.

6. The in vitro method as claimed in claim 1, characterized in that nuclear magnetic resonance (NMR) methods, biochemical, enzymatic, immunological, clinical-chemical, chromatographic, mass spectrometric, electrochemical, photometric methods are applied to determine choline, choline and/or trimethyl ammonium derivatives selected from the group comprising phosphoryl choline, plasmalogens, and lysoplasmenyl choline (CCTD), and/or the reaction products thereof selected from the group comprising 1-O-alk-1'-enyl-2 substituted glycerol and 1-O-alk-1'-enyl-2 substituted glycerol phosphate.

7. An in vitro method of recognizing and diagnosing acute coronary syndromes, generally when there is suspicion of an acute coronary syndrome, namely an acute myocardial infarction and/or severe forms of unstable angina pectoris involving myocardial micronecrosis, characterized in that body fluids or component parts of the body are subjected to NMR spectroscopy and the evaluation is accomplished by pattern recognition of a plurality of substances, especially of choline, choline and/or trimethyl ammonium derivatives selected from the group comprising phosphoryl choline, plasmalogens, and lysoplasmenyl choline (CCTD), of the reaction products thereof selected from the group comprising 1-O-alk-1'-enyl-2 substituted glycerol and 1-O-alk-1'-enyl-2 substituted glycerol phosphate, and of creatine and dimethyl amine, wherein an increase in CCTD and/or reaction products of CCTD causes the diagnosis of acute coronary syndromes, namely an acute myocardial infarction and/or severe forms of unstable angina pectoris involving myocardial micronecrosis.

8. The in vitro method as claimed in claim 1, characterized by determining choline, choline and/or trimethyl ammonium derivatives selected from the group comprising phosphoryl choline, plasmalogens, and lysoplasmenyl choline, and/or the reaction products thereof selected from the group comprising 1-O-alk-1'-enyl-2 substituted glycerol and 1-O-alk-1'-enyl-2 substituted glycerol phosphate in a body fluid selected from a group comprising serum, plasma, whole blood, prepared blood sample, and urine.

9. A test kit for diagnosis and/or analysis of acute coronary syndromes, generally when there is suspicion of an acute coronary syndrome, namely, an acute myocardial infarction and/or severe forms of unstable angina pectoris involving myocardial micronecrosis, characterized by comprising means for receiving a body fluid or a component part of a body and means for detecting choline, choline and/or trimethyl ammonium derivatives selected from the group comprising phosphoryl choline, plasmalogens, and lysoplasmenyl choline, and/or the reaction products thereof selected from the group comprising 1-O-alk-1'-enyl-2 substituted glycerol and 1-O-alk-1'-enyl-2 substituted glycerol phosphate in the body fluid or component part of the body, wherein an increase in CCTD and/or reaction products of CCTD causes the diagnosis of acute coronary syndromes, namely an acute myocardial infarction and/or severe forms of unstable angina pectoris involving myocardial micronecrosis.

10. The test kit as claimed in claim 9, characterized in that the means for detecting give an indication when a limit value for the content of choline, choline and/or trimethyl ammonium derivatives selected from the group comprising phosphoryl choline, plasmalogens, and lysoplasmenyl choline, and/or the reaction products thereof selected from the group comprising 1-O-alk-1'-enyl-2 substituted glycerol and 1-O-alk-1'-enyl-2 substituted glycerol phosphate in the body fluid or component part of the body is exceeded.

11. An in vitro method for recognizing and diagnosing an acute myocardial infarction in a patient for whom an acute myocardial infarction is suspected, said in vitro method comprising the steps of:
   (a) determining the level of CCTD in a body fluid sample from said patient said CCTD consisting of choline, choline and/or trimethyl ammonium derivatives selected from the group consisting of phosphoryl choline, plasmalogens and lysoplasmenyl choline; and
   (b) comparing said CCTD level in said body fluid sample to appropriate standards to determine whether or not an acute myocardial infarction is present in said patient.

12. An in vitro method for recognizing and diagnosing a severe form of unstable angina pectoris in a patient for whom a severe form of unstable angina pectoris is suspected, said in vitro method comprising the steps of:
   (a) determining the level of CCTD in a body fluid sample from said patient, said CCTD consisting of choline, choline and/or trimethyl ammonium derivatives selected from the group consisting of phosphoryl choline, plasmalogens and lysoplasmenyl choline; and
   (b) comparing said CCTD level in said body fluid sample to appropriate standards to determine whether or not a severe form of unstable angina pectoris is present in said patient.

13. The in vitro method as claimed in claim 12 wherein said CCTD consists of choline.

14. An in vitro method of recognizing and diagnosing, when an acute coronary syndrome is suspected, an acute myocardial infarction and/or severe forms of unstable angina pectoris, characterized by determining the content of choline, choline and/or trimethyl ammonium derivatives selected from the group comprising phosphoryl choline, plasmalogens, and lysoplasmenyl choline (CCTD) in body fluids or component parts of the body wherein an increase in CCTD causes the diagnosis of an acute myocardial infarction and/or severe forms of unstable angina pectoris.

* * * * *